(12) United States Patent
Dyer et al.

(10) Patent No.: US 6,688,421 B2
(45) Date of Patent: Feb. 10, 2004

(54) EARMOLD FOR IMPROVED RETENTION OF COUPLED DEVICE

(75) Inventors: Medford Alan Dyer, San Diego, CA (US); Daniel Wayne Mauney, Austin, TX (US); Thomas Henry Perszyk, San Diego, CA (US); Edward Daniel Springer, Chula Vista, CA (US)

(73) Assignee: Jabra Corporation, San Diego, CA (US)

( * ) Notice: Subject to any disclaimer, the term of this patent is extended or adjusted under 35 U.S.C. 154(b) by 0 days.

(21) Appl. No.: 10/125,850

(22) Filed: Apr. 18, 2002

(65) Prior Publication Data

US 2003/0196850 A1 Oct. 23, 2003

(51) Int. Cl.[7] .............................................. H04R 25/02
(52) U.S. Cl. ................... 181/130; 181/135; 381/68.6; 381/69
(58) Field of Search ............................... 206/482, 477, 206/478; 381/68.6, 69; 181/128–135

(56) References Cited

U.S. PATENT DOCUMENTS

| | | | | | |
|---|---|---|---|---|---|
| 1,343,651 | A | * | 6/1920 | Stafford | 442/85 |
| 1,388,561 | A | * | 8/1921 | Grote | 76/89.2 |
| 1,644,963 | A | * | 10/1927 | Ulich | 206/278 |
| 3,567,058 | A | * | 3/1971 | Mascia | 215/213 |
| 5,659,156 | A | * | 8/1997 | Mauney et al. | 181/130 |
| 6,009,998 | A | * | 1/2000 | Webinger | 206/364 |
| 6,122,388 | A | * | 9/2000 | Feldman | 381/322 |
| 6,543,615 | B2 | * | 4/2003 | Lake | 206/371 |

* cited by examiner

*Primary Examiner*—Robert Nappi
*Assistant Examiner*—David S Warren
(74) *Attorney, Agent, or Firm*—Bingham McCutchen LLP; David G. Beck (57) ABSTRACT

An earmold, including retention flaps to more securely hold an audio device coupled to the earmold, is provided. In some embodiments, the audio device includes both a microphone and a speaker while in other embodiments the audio device is a speaker associated with a portable audio system.

13 Claims, 10 Drawing Sheets

EARMOLD FOR IMPROVED RETENTION OF COUPLED DEVICE

FIELD OF THE INVENTION

The present invention relates to the field of devices used to hold audio devices at the opening of a user's ear.

BACKGROUND OF THE INVENTION

Various types of earmolds are manufactured in the prior art, primarily for use with hearing aids, communication devices and portable audio systems. Most existing earmolds rely on a deep and tight insertion into the ear canal for providing stability of the device in the ear. This type of deep and tight insertion tends to cause painful rubbing of the insert against the ear canal and also can have the effect of sealing the ear canal. As a result, the user experiences irritation and discomfort, particularly after many consecutive hours or days of use. Sealing the ear canal has dangerous implications to the wearer. It will also affect a person's ability to hear ambient sound by reducing the intensity of the sound. It will alter a person's ability to localize sound, particularly in the high frequencies where interaural sound pressure differences are the primary cue for localization.

U.S. Pat. No. 5,659,156 ("the '156 patent") solves most of the foregoing problems of such prior art devices. However, the earmolds disclosed in the '156 patent sometimes come loose from the speaker, communication device, hearing aid, etc. (referred to herein as an "audio device") to which they are coupled.

SUMMARY OF THE INVENTION

The present invention addresses numerous shortcomings of prior art earmolds. Preferred earmolds according to the invention include a first protrusion to secure the earmold to a user's ear, a cavity shaped on a first side to receive an audio device and shaped on a second side to fit within the user's outer ear (a "second protrusion"), and at least one retention flap for securely retaining the audio device.

Preferred embodiments include two or more retention flaps disposed around the perimeter of the first side of the cavity. Preferably, the retention flaps do not extend around the entire perimeter of the cavity, but instead are discontinuous. Such discontinuity allows for easier insertion and removal of the audio device, while holding the audio device more securely than earmolds of the prior art. These retention flaps may be formed in a variety of shapes, including but not limited to arcuate shapes, triangular shapes and trapezoidal shapes.

In some preferred embodiments, a user engages the first protrusion of the earmold by inserting the earmold into the ear and then rotating the mold so that this first protrusion rests under the crus of the helix of the ear. In other embodiments, the first protrusion contacts a different portion of the outer ear.

The second protrusion conveys sound from the speaker into the user's ear canal. Preferred embodiments of the second protrusion require only a very shallow insertion (approximately ⅛ inch in some embodiments) into the user's ear canal. In some embodiments, the earmold is held in place by the first protrusion and/or other features such that the second protrusion does not contact the ear canal. In other embodiments, the second protrusion lightly contacts a portion of the ear canal. In yet other embodiments, the second protrusion contacts opposing sides of the ear canal.

Preferably, no seal is formed between the second protrusion and the ear canal. Accordingly, some preferred embodiments of the second protrusion include an ear canal insert vent on the second side to prevent a pneumatic seal from being formed in the ear. Some preferred embodiments include a sound bore which penetrates from the first side through to the second side. Accordingly, when these embodiments of the invented earmold are used, complete occlusion of the ear canal is prevented, thereby minimizing the amount by which a person's ability to hear ambient sound is diminished when wearing the inventive earmold. As a result, a person's ability to localize sound is maintained.

The invented earmold's profile follows the curvature of the ear canal. By following the curvature of the ear canal, the user's comfort is greatly improved. Moreover, preferred embodiments of the present invention include a notch in the earmold which provides relief to a user's antitragus. Relief to the antitragus is important to prevent compression of tissue at the antitragus and to avoid associated discomfort.

Some preferred embodiments include markings for reference by the wearer to ensure proper orientation of an audio device.

Some preferred earmolds are composed of soft plastic material and others are composed of an elastomeric material or other material. Some preferred earmolds are composed of polyvinyl and/or silicone.

Some embodiments of the present invention provide an earmold for holding an audio device near a user's ear, the user's ear comprising an ear canal and an outer ear, the earmold including: a cavity formed in a first side of the earmold, the cavity configured to receive at least a portion of the audio device; a first protrusion extending from a second side of the earmold and configured to engage a portion of the user's outer ear; a second protrusion extending from the second side of the earmold and configured to be positioned proximate the user's ear canal; and a plurality of retention flaps extending from an edge of the cavity towards an interior of the cavity to secure at least a portion of the audio device within the cavity, the retention flaps extending around only a portion of a circumference of the cavity. The inventive earmold preferably includes a sound bore having a first end inside the cavity and a second end proximate a tip of the second protrusion.

Some such earmolds include a vent disposed along a portion of the second protrusion. Some such vents extend from the edge of the cavity to a point proximate a tip of the second protrusion. In some embodiments, the first protrusion is configured to engage under a crus of a helix of the outer ear.

Some embodiments include an alignment notch which allows a user to orient the audio device with respect to the earmold. The retention flaps may be formed on opposing sides of the edge of the cavity or may have other configurations. An alignment notch may be formed in a retention flap.

In some embodiments, a notch is provided which is configured to provide contact relief to an antitragus of the user. In some embodiments, the earmold is configured to prevent the second protrusion from touching the ear canal and in other embodiments the earmold is configured to hold the second protrusion in contact with the ear canal.

DESCRIPTION OF THE SPECIFIC EMBODIMENTS

Figure 1:
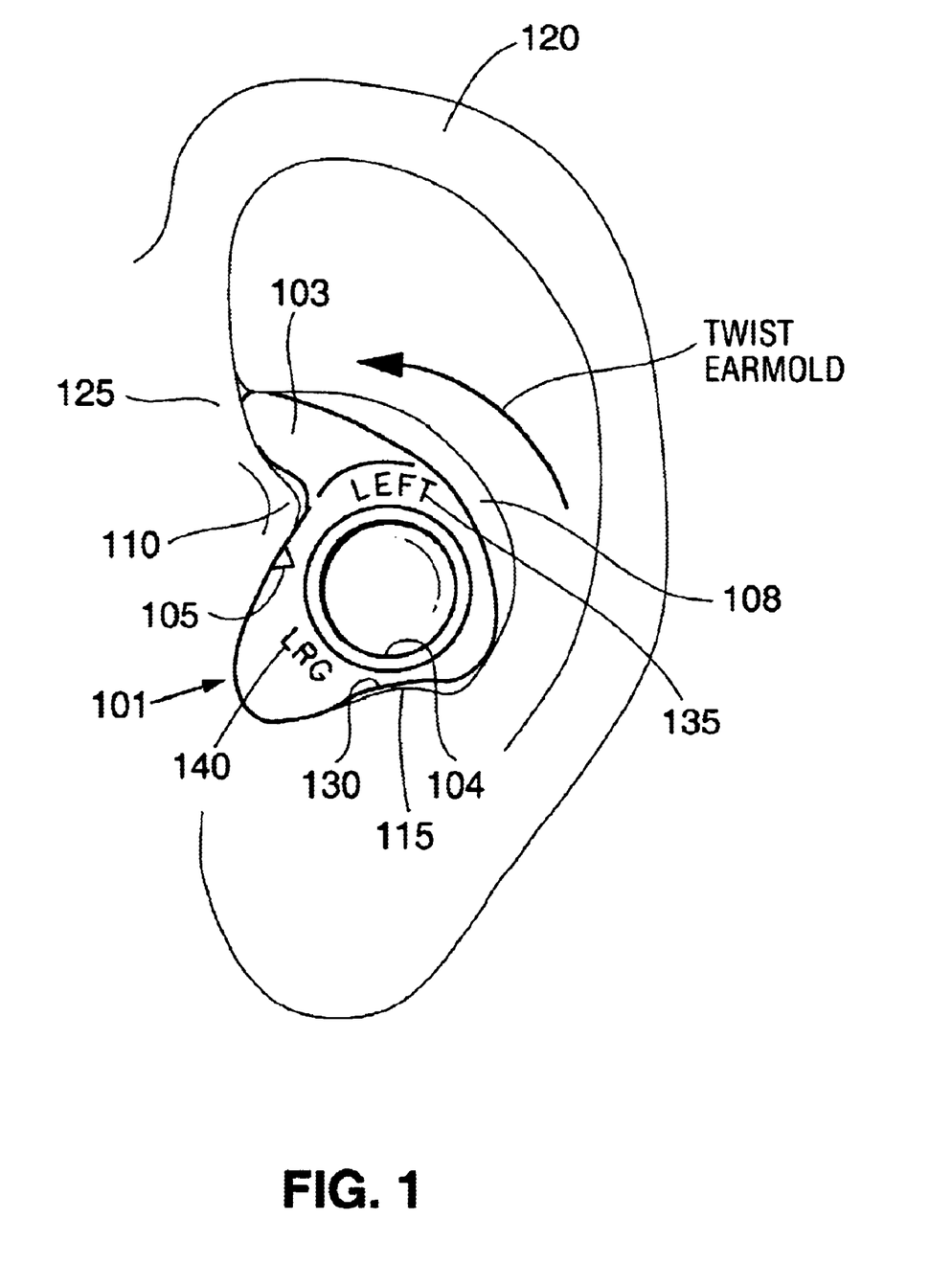
FIG. 1 depicts one preferred embodiment of a left earmold of the present invention installed in a human ear.

FIG. 1 shows one preferred embodiment of left earmold 101 inserted at the opening of a human ear. Left earmold 101 is disposed within concha 108, which is the largest cavity in the outer ear, and between tragus 110 and antitragus 115. Helix 120 begins at crus 125 and wraps around most of the outer ear.

Left earmold 101 is held in place in the ear, at least in part, by first protrusion 103. Left earmold 101 includes receptacle or cavity 104 to accommodate at least a portion of an audio device.

Optional vent or notch 105 prevents a pneumatic seal from forming in the ear canal. Vent 105 also accommodates the transmission of sound into the ear canal from the user's surroundings.

Optional antitragus notch 130 spreads out the surface area over which the weight of left earmold 101 bears upon antitragus 115. Accordingly, antitragus notch 130 causes less pressure on antitragus 115 and results in greater comfort to the user. In some preferred embodiments, antitragus notch 130 is generally smooth and slightly concave in shape, as depicted in FIG. 1. However, antitragus notch 130 has different shapes in various embodiments of the inventive earmold, and may be, for example, only a subtle change in curvature of a convex portion of the earmold.

The embodiment illustrated in FIG. 1 includes optional labels 135 and 140 to indicate the intended ear (left ear) and the size of the mold (large), respectively.

Figure 2:
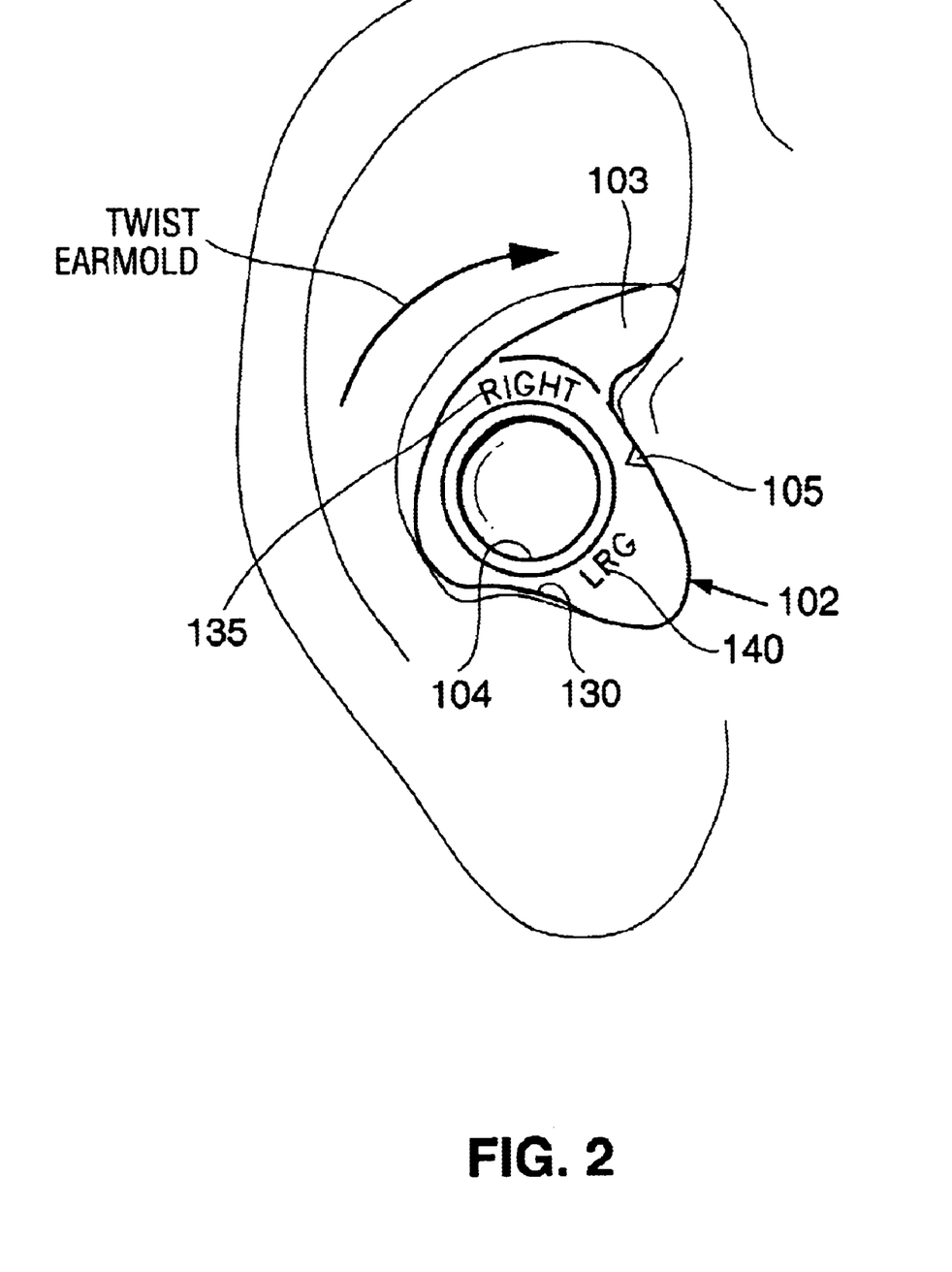
FIG. 2 depicts one preferred embodiment of a left earmold of the present invention installed in a human ear.

FIG. 2 shows a preferred right earmold 102 inserted at the opening of a human ear. Right earmold 102 generally corresponds to left earmold 101 of FIG. 1. Right earmold 102 includes first protrusion 103 for holding right earmold 102 in the ear, receptacle 104 to accommodate at least a portion of an audio device, optional antitragus notch 130, optional vent 105 and optional labels 135 and 140. It can be seen from FIGS. 1 and 2 that the shape and size of the invented earmold is selected to match and fit within the user's outer ear, including the shape of the user's tragus, antitragus, concha and crus.

Figure 3:
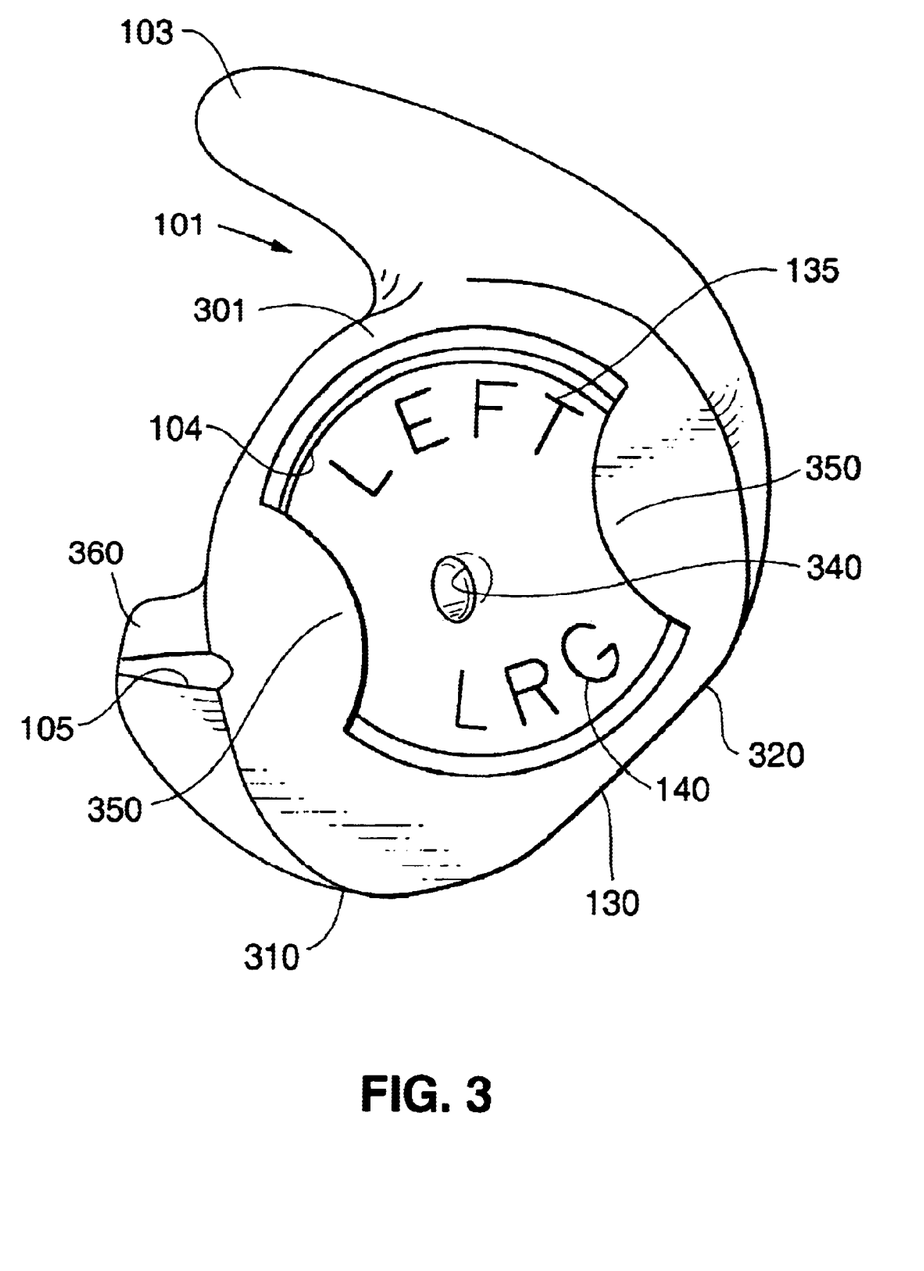
FIG. 3 depicts an embodiment of a left earmold of the present invention.

FIG. 3 shows a first side of left earmold 101. The bottom 320 of left earmold 101 and antitragus notch 130 are shown. In this embodiment, antitragus notch 130 is not concave, but instead is a slightly flattened portion of an otherwise convex surface.

Cavity or receptacle 104 is provided to accommodate at least a portion of an audio device. In some embodiments, receptacle 104 is located on the approximate center of the first side of earmold 101, the second side of the earmold being defined as the side of the earmold adjacent to the user's ear. In one preferred embodiment of the invention, cavity 104 is dome-shaped, with the shallowest part of cavity 104 being 0.1050 inches deep at the outer edge and the crest of the dome extending another 0.070 inches in the center of cavity 104. One preferred cavity 104 is circular in shape and approximately 0.5 inches in diameter.

Sound bore 340 extends from cavity 104 to the tip of second protrusion 360 (not shown). Sound bore 340 provides a port through which sound can travel from the speaker part of the audio device to the ear canal of the user. Sound bore 340 also allows air to pass between cavity 104 and the wearer's ear canal. In one preferred embodiment, sound bore 340 is 0.10 inches in diameter and is close to the center of second protrusion 360. The center of one such bore 340 is 0.090±0.030 inches from the edge of cavity 104.

FIG. 3 illustrates an embodiment of retention flaps 350 according to the present invention. Retention flaps 350 protrude from the edges of cavity 104 in order to retain more securely an audio device (not shown) which has been disposed within cavity 104. This feature will be more fully appreciated with reference to FIGS. 5, 8 and 10. In this example, retention flaps 350 are arcuate in shape. In other embodiments, retention flaps 350 are formed in a variety of shapes, including but not limited to the shapes indicated in FIGS. 4–6 and 8–10.

The embodiment shown in FIG. 3 illustrates optional notch 105, which is gas-communicative with a user's ear canal. Notch 105 prevents a pneumatic seal from being formed in the ear canal and allows a user to hear ambient sounds.

Also shown is lower lobe 310 and first protrusion 103. Left earmold 101 is kept in place in the ear by the combination of first protrusion 103 and features found on the second side of left earmold 101, preferably with the assistance of contact, even if slight, by lower lobe 310, bottom 320 and antitragus notch 130.

Figure 4:
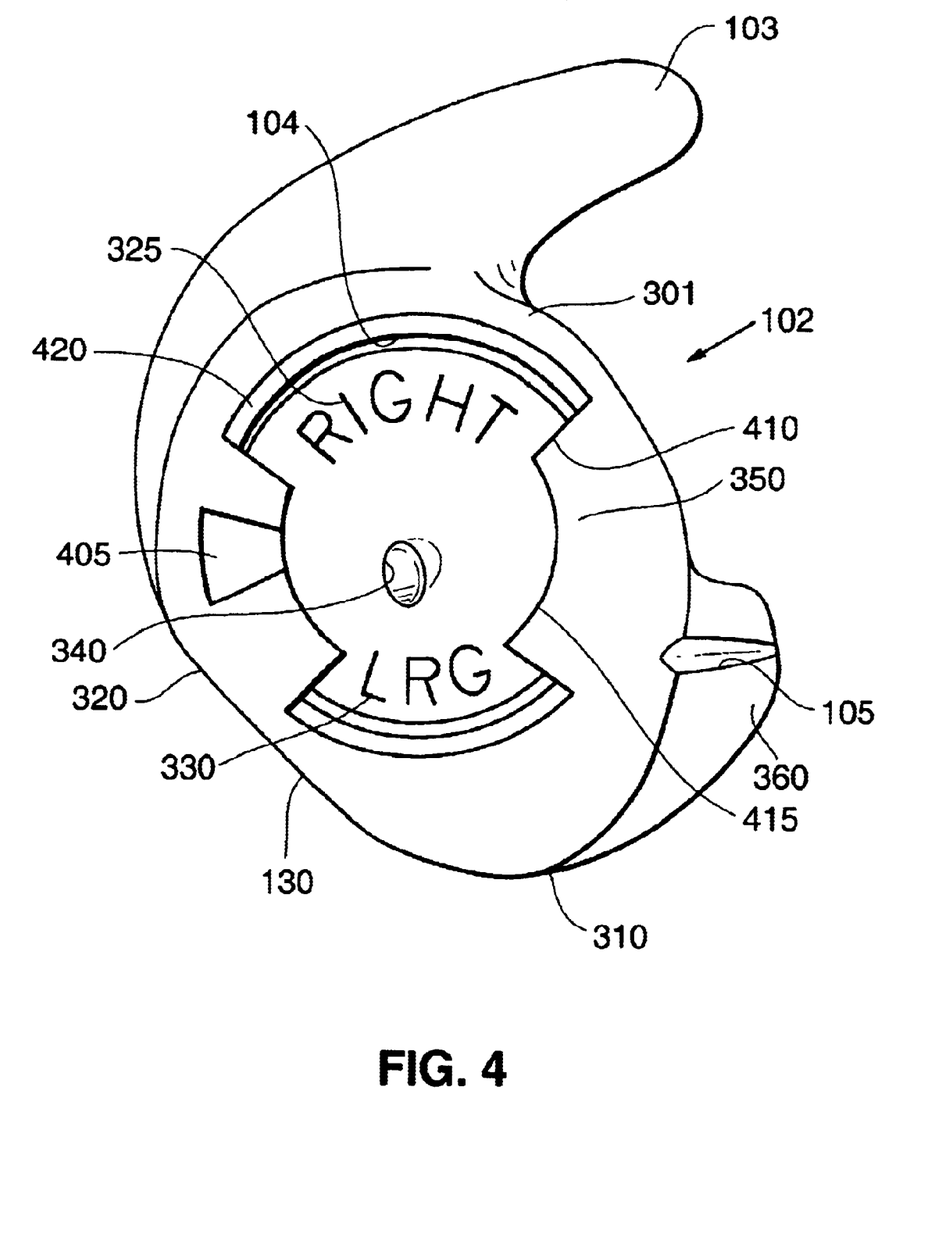
FIG. 4 depicts an embodiment of a right earmold of the present invention.

The description of FIG. 4 parallels that of FIG. 3, but for a right earmold with different retention flaps 350. FIG. 4 shows a first side of right earmold 102. Bottom 320 of right earmold 102 and antitragus notch 130 are shown.

Cavity or receptacle 104 accommodates at least a portion of an audio device. Receptacle 104 is located on a first side of earmold 102. A second side of earmold 102 is adjacent to the user's ear. A portion of second protrusion 360 and optional vent 105 may be seen on the second side of earmold 102. In some preferred embodiments of the invention, cavity 104 is a truncated cylinder, with the walls of the cylinder being between ⅛ and ¼ inches deep.

In the embodiment shown in FIG. 4, retention flaps 350 extend from opposing sides of cavity 104 to hold an audio device more securely within cavity 104. In this embodiment, retention flaps 350 include sides 410 which project towards the interior of cavity 104 and sides 415 which roughly parallel edge 420 of cavity 104.

Optional alignment mark 405 has been formed in one retention flap 350 to indicate to a user the proper orientation of an audio device in right earmold 102. Preferably, alignment mark 405 may easily be detected by touch, so that a user may orient an audio device with reference to alignment mark 405 after the earmold is secured within the user's ear. Some audio devices manufactured by Jabra Corporation, the present assignee, are made with a tab, notch or similar structure which corresponds to the position of alignment mark 405.

Optional notch 105 prevents a pneumatic seal from being formed in the ear canal and allows a user to hear more ambient sounds than would be possible if a seal were formed.

Also shown in FIG. 4 are lower lobe 310 and first protrusion 103. Right earmold 102 is kept in place in the ear by the combination of first protrusion 103 and features found on the second side of right earmold 102, preferably with the assistance of contact, even if slight, by lower lobe 310, antitragus notch 130 and bottom 320. Preferred embodiments require only a very shallow insertion (approximately ⅛ inch in some embodiments) of the second protrusion into the user's ear canal.

In some embodiments, the earmold is held in place by the first protrusion and/or other features such that the second protrusion does not contact the ear canal. In other embodiments, the second protrusion lightly contacts a portion of the ear canal, e.g., a lower side edge of the ear canal. In yet other embodiments, the second protrusion contacts opposing sides of the ear canal and/or contacts most or all of the circumference of the ear canal.

Optional labels 325 and 330 indicate the intended ear (the right ear) and the size of the mold (large), respectively.

Figure 5:
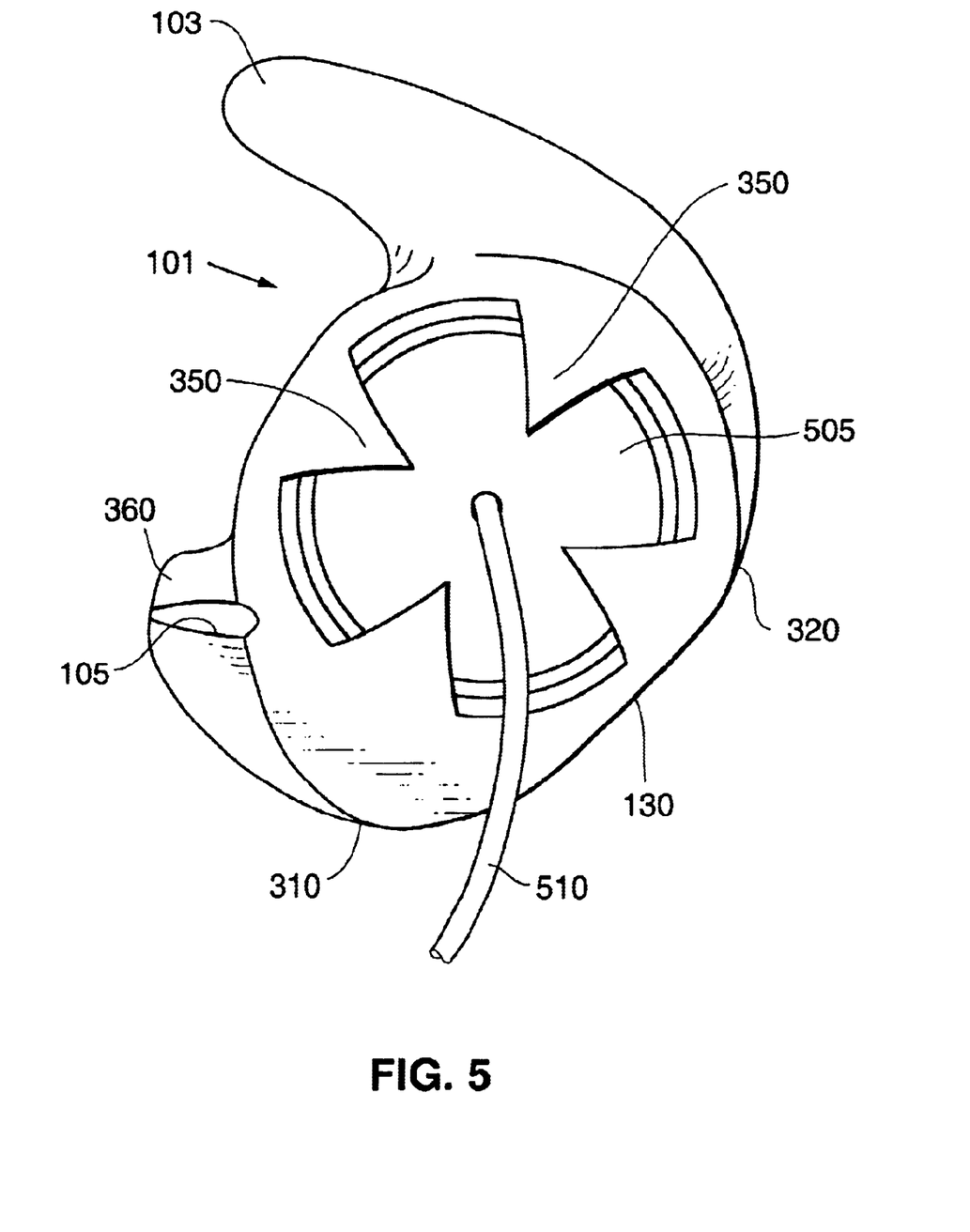
FIG. 5 depicts an embodiment of a left earmold with an earphone installed therein.

FIG. 5 shows left earmold 101 with audio device 505 installed. In this embodiment, retention flaps 350 are roughly triangular in shape, with the free vertex of each triangle extending towards the approximate center of cavity 104. Cord 510 provides power and/or a signal for audio device 505. Notch 105, first protrusion 103, lower lobe 310, bottom 320, and antitragus notch 130 are shown.

Figure 6:
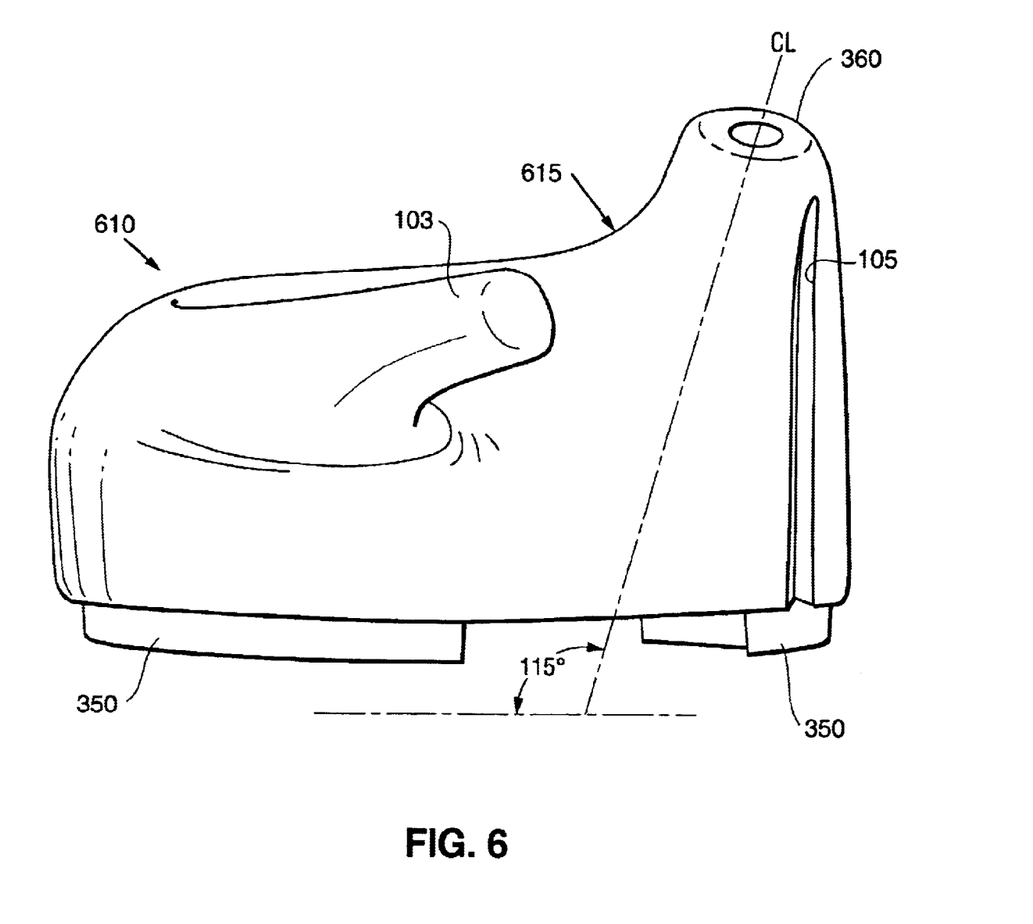
FIG. 6 depicts a side view of one embodiment of the invented earmold.

FIG. 6 is a side view of one preferred earmold. Second protrusion 360 extends upward from the base of second side 610 of the earmold. In some embodiments, second protrusion 360 extends upward at an angle of approximately 115 degrees from the horizontal, to closely match the curvature of the user's ear canal. In preferred embodiments, the insertion depth of second protrusion 360 is shallow, for the purpose of minimizing or eliminating physical contact with the inner ear canal. In some such embodiments, the insertion depth of second protrusion 360 is kept to ⅛ inch or less.

As noted above, vent 105 is provided to prevent a pneumatic seal from forming in the ear. In one preferred embodiment, vent 105 is 0.090 inches wide and 0.045 inches deep with curved edges inside and outside the vent. Vent 105 extends from the first side of the earmold up the side of second protrusion 360. In some preferred embodiments, vent 105 ends no less than 0.10 inches from the end of the second protrusion 360.

Second protrusion 360 is angled back or curved by an amount approximating the concha angle of the a user's ear. The purpose of this angle 615 is to permit a closer, more comfortable fit with the ear.

In the embodiment shown in FIG. 6, retention flaps 350 are similar in shape to those depicted in FIG. 4. Retention flaps 350 extend only part of the way around the circumference of cavity 104, in order to allow an audio device to be more easily inserted into, or removed from, cavity 104.

Figure 7:
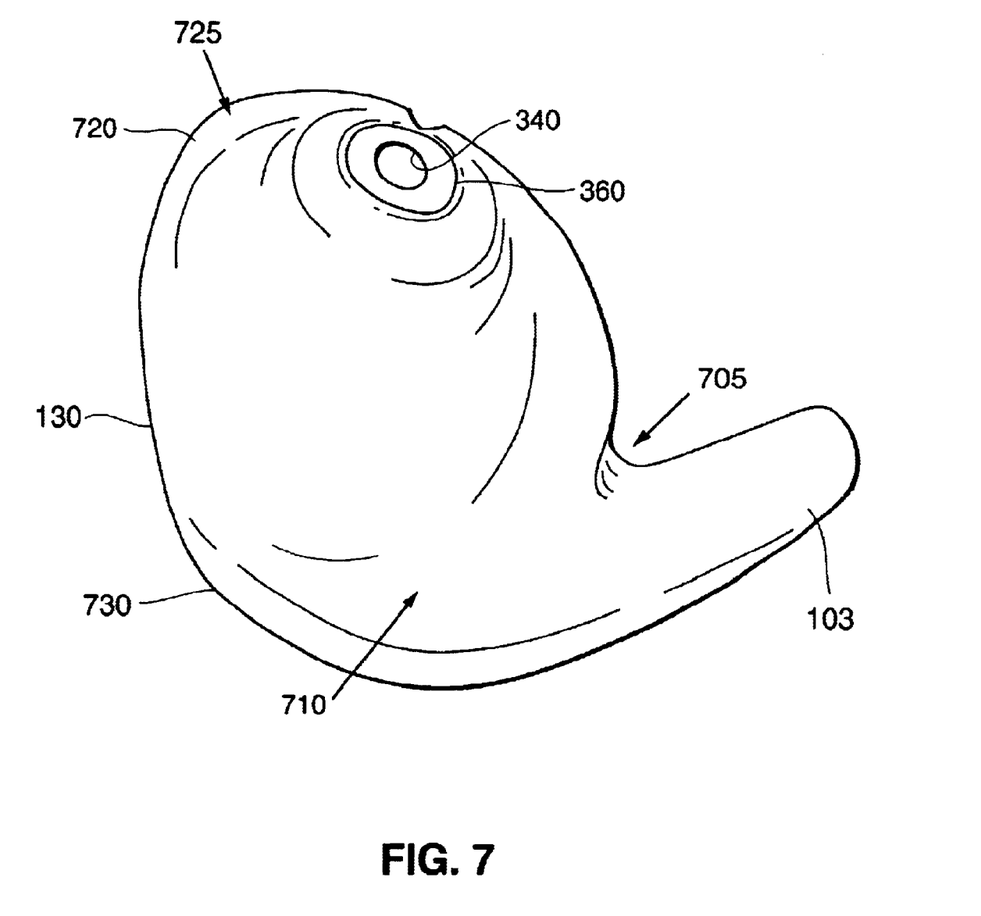
FIG. 7 depicts a top view of one embodiment of the invented earmold.

Referring to FIG. 7, a top view of a preferred earmold is shown. First protrusion 103 is designed to fit comfortably under the crus of helix of a user's outer ear. Valley 705 exists between first protrusion 103 and second protrusion 360. The purpose of valley 705 is to more naturally fit the contours of the outer ear and to achieve user comfort.

Optional concha dehump 710 is included in the lower center of the second side to permit a close fit with the outer ear. Optional antitragus notch 130 is also included in the design of the earmold to relieve pressure on the user's antitragus. Shoulder 720 is also provided in the region of the lower lobe 725 for a better fit with the edge of a user's concha. Also depicted is the bottom 730. Retention flaps 350 are present, but are not visible in FIG. 7.

Figure 8:
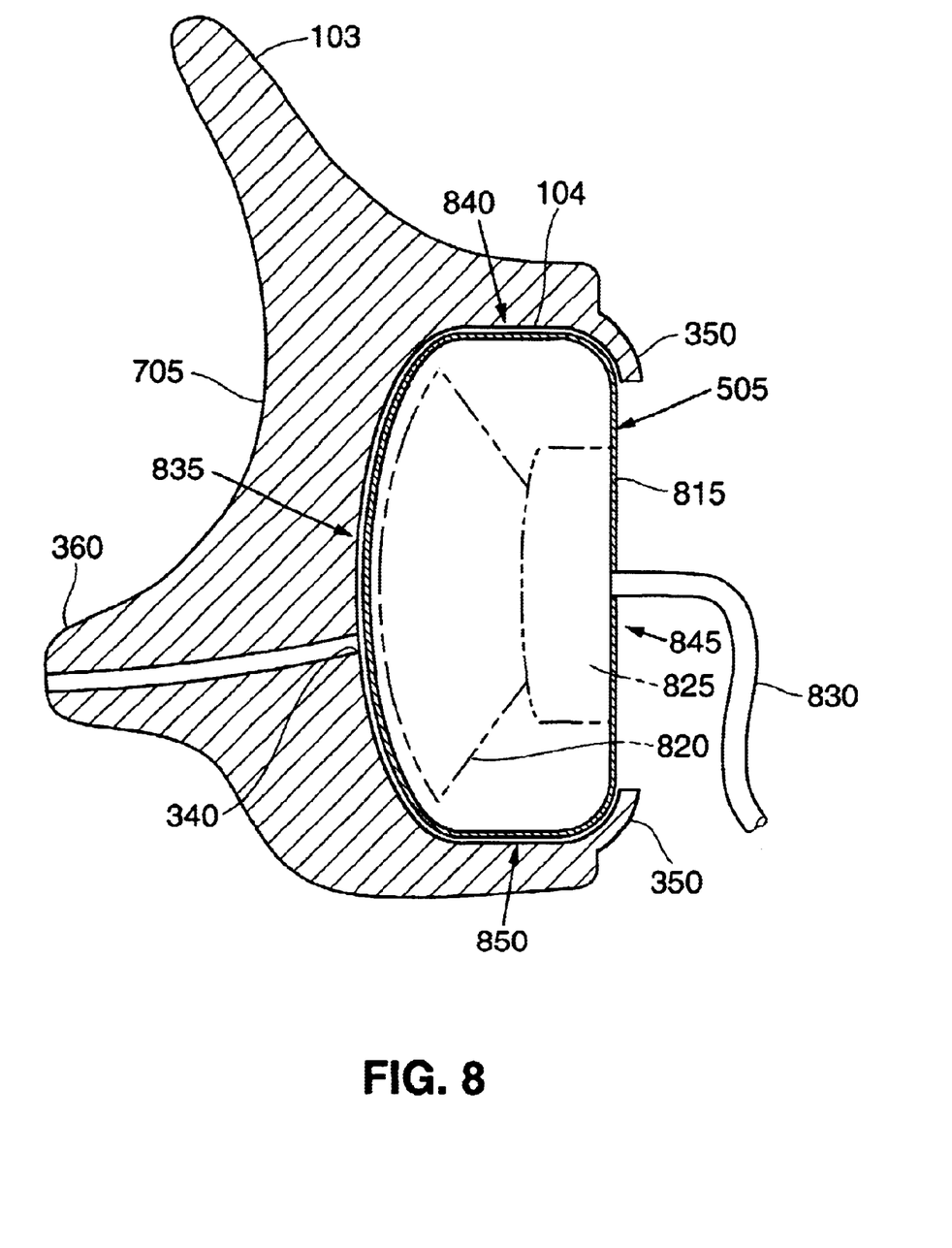
FIG. 8 depicts a cross-section of one embodiment of the invented earmold.

FIG. 8 is a cut-away view of a preferred earmold and an audio device. Audio device 505 includes speaker 820 and magnet 825, enclosed within case 815. Depending on the embodiment, cord 830 may conduct signals to control speaker 820 and/or supply power to audio device 505.

In this embodiment, audio device 505 fits snugly into cavity 104, with very little space remaining around the edges. Front portion 835, top portion 840 and bottom portion 850 of audio device 505 preferably conform with the corresponding inner surfaces of cavity 104. It is convenient, though not necessary, for at least a portion of audio device 505 to fit closely with the interior of cavity 104. If only top portion 840 and bottom portion 850 of audio device 505 fit snugly within cavity 104, audio device 505 should be adequately secured by the friction between these portions and cavity 104 and by retention flaps 350.

Retention flaps 350 extend towards the center of back portion 845 of audio device 505 and towards the interior of cavity 104. Here, retention flaps 350 do not extend as far towards the interior of cavity 104 as in other embodiments described in the previous paragraphs. Nonetheless, even the relatively short retention flaps 350 illustrated in FIG. 8 can hold audio device 505 firmly in place. There is a tradeoff with respect to the length of retention flaps 350: other factors being equal, the longer retention flaps 350 are made, the more securely they can hold an audio device. However, longer retention flaps 350 tend to interfere more with the processes of inserting audio device 505 into cavity 104 and extracting audio device 505 from cavity 104.

As illustrated in FIG. 8, sound from speaker 820 is conducted from a first end of sound bore 340 within cavity 104 to a second end of sound bore 340 at or near the tip of second protrusion 360. As noted above, the tip of second protrusion 360 is disposed at the opening of a user's ear canal. Accordingly, sound bore 340 facilitates the transmission of sound from speaker 820 to a user's ear canal.

Figure 9:
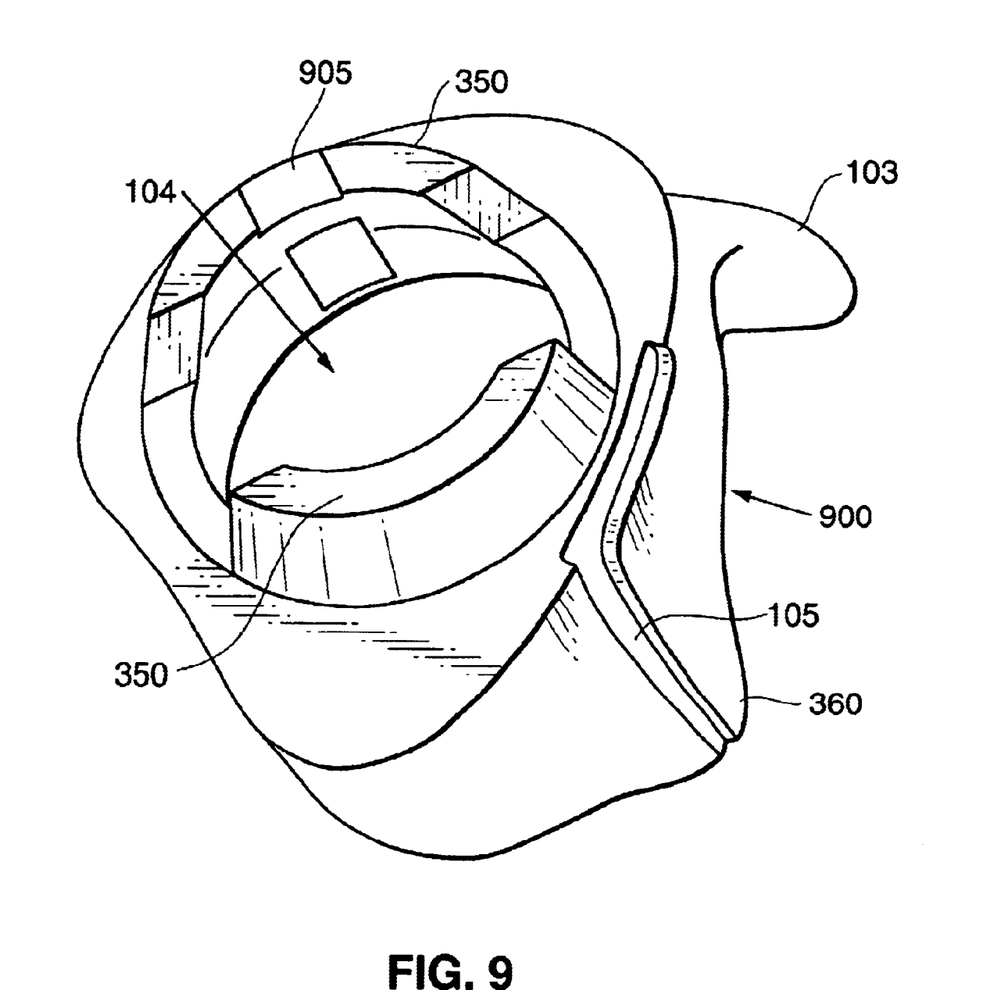
FIG. 9 depicts another embodiment of the invented earmold.

FIG. 9 depicts another embodiment of an earmold according to the present invention. Retention flaps 350 are formed along opposing sides of cavity 104 on the first side of earmold 900. Alignment mark 905 is formed in one of retention flaps 350 and extends into cavity 104. Alignment mark 905 allows a user to orient an audio device within cavity 104 by "feel" as well as by inspection of earmold 900.

Vent 105 extends from the edge of the first side of earmold 900 to a point near the tip of second protrusion 360 on the second side of earmold 900. In this embodiment, vent 105 extends part of the way around the circumference of the first side of earmold 900.

Figure 10:
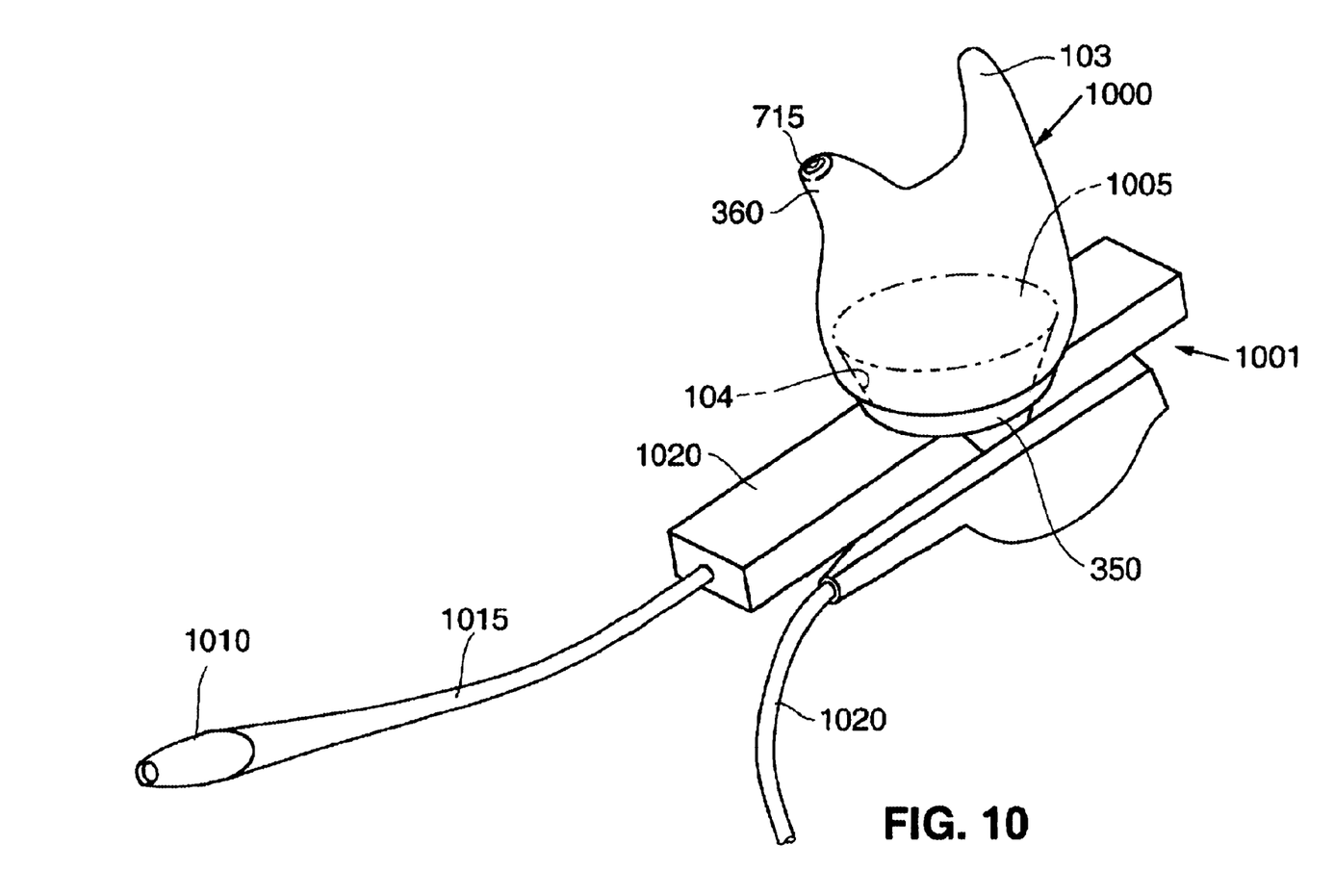
FIG. 10 depicts an embodiment of the invented earmold attached to a two-way communication device.

FIG. 10 illustrates how some embodiments of the present invention may be formed to accommodate a portion of an audio device having a speaker and a boom microphone. Earmold 1000 is shown engaged with two-way communication device 1001. Speaker 1005, shown in phantom, is disposed within cavity 104. Microphone 1010 is supported by boom 1015, which fits into support 1020. Retention flaps 350 extend past speaker 1005 to engage a portion of support 1020.

First protrusion 103 engages with a portion of a user's outer ear and second protrusion 360 fits into a user's ear canal. Sound bore 340 extends from cavity 104 in the first side of earmold 1000 to the tip of second protrusion 360 on the second side of earmold 1000. Sound bore 340 provides a port through which sound can travel from speaker 1005 to the user's ear canal. Sound bore 340 also allows air to pass between cavity 104 and the wearer's ear canal.

In some embodiments, cord 1020 supplies power to two-way communication device 1001. In some such embodiments, two-way communication device 1001 includes a transceiver (not shown) which receives first signals from microphone 1010 and transmits the first signals to an external device, and which receives second signals from an external device and transmits the second signals to speaker 1005. In other embodiments, cord 1020 transmits first signals from microphone 1010 to an external device and transmits second signals from an external device to speaker 1005. In some preferred embodiments, the external device is a telephone, such as a cellular telephone. In other embodiments, the external device is a personal digital assistant, a computer, or a similar device.

While the best mode for practicing the invention has been described in detail, those of skill in the art will recognize that there are numerous alternative designs, embodiments, modifications and applied examples that are within the scope of the present invention. For example, in some alternative embodiments of the invention, the earmold does not include the second protrusion which penetrates (although not deeply) the ear canal. The second protrusion can be omitted and secure mounting to an ear can still be achieved. Accordingly, the scope of this invention is not limited to the previously described embodiments.

We claim:

1. An earmold for holding an audio device near a user's ear, the user's ear comprising an ear canal and an outer ear, the earmold comprising:
   a cavity formed in a first side of the earmold, the cavity configured to receive at least a portion of the audio device;
   a first protrusion extending from a second side of the earmold and configured to engage a portion of the user's outer ear;
   a second protrusion extending from the second side of the earmold and configured to be positioned proximate the user's ear canal;
   a sound bore having a first end inside the cavity and a second end proximate a tip of the second protrusion; and
   a plurality of retention flaps extending from an edge of the cavity towards an interior of the cavity to secure at least a portion of the audio device within the cavity, the retention flaps extending around only a portion of a circumference of the cavity.

2. The earmold of claim 1, further comprising a vent disposed along a portion of the second protrusion.

3. The earmold of claim 1, wherein the first protrusion is configured to engage under a crus of a helix of the outer ear.

4. The earmold of claim 1, further comprising an alignment notch which allows a user to orient the audio device with respect to the earmold.

5. The earmold of claim 1, wherein the retention flaps are formed on opposing sides of the edge of the cavity.

6. The earmold of claim 1, further comprising a notch configured to provide contact relief to an antitragus of the user.

7. The earmold of claim 1, wherein the earmold is configured to prevent the second protrusion from touching the ear canal.

8. The earmold of claim 1, wherein the earmold is configured to hold the second protrusion in contact with at least a portion of the ear canal.

9. The earmold of claim 2, wherein the vent extends from the edge of the cavity to a point proximate a tip of the second protrusion.

10. The earmold of claim 4, wherein the alignment notch is formed in a retention flap.

11. An earmold for holding an audio device near a user's ear, the user's ear comprising an ear canal and an outer ear, the earmold comprising:
    a cavity formed in a first side of the earmold, the cavity configured to receive at least a portion of the audio device;
    a first protrusion extending from a second side of the earmold and configured to engage under a crus of a helix of the outer ear;
    a second protrusion extending from the second side of the earmold and configured to be held proximate the user's ear canal;
    a vent extending from an edge of the cavity to a point proximate a tip of the second protrusion;
    a sound bore having a first end inside the cavity and a second end proximate a tip of the second protrusion;
    a plurality of retention flaps extending from opposing sides of the edge of the cavity towards an interior of the cavity to secure at least a portion of the audio device within the cavity, the retention flaps extending around only a portion of a circumference of the cavity;
    an antitragus notch configured to provide contact relief to an antitragus of the user; and
    an alignment notch which allows a user to orient the audio device with respect to the cavity.

12. The earmold of claim 11, wherein earmold is configured to prevent the second protrusion from touching the ear canal.

13. The earmold of claim 11, wherein earmold is configured to hold the second protrusion in contact with at least a portion of the ear canal.

* * * * *